(12) United States Patent
Rosani et al.

(10) Patent No.: US 9,733,624 B2
(45) Date of Patent: Aug. 15, 2017

(54) METHOD FOR CORRECTIVE ACTION ON THE OPERATION OF A LINE FOR THE PRODUCTION OF ABSORBENT SANITARY ARTICLES, SUCH AS NAPPIES FOR BABIES OR INCONTINENCE PADS FOR ADULTS, SANITARY TOWELS OR THE LIKE

(75) Inventors: Marco Rosani, Vailate (IT); Gabriele Pastrello, Milan (IT); Matteo Piantoni, Albino (IT); Alberto Perego, Milan (IT)

(73) Assignee: GDM S.p.A., Bologna (IT)

( * ) Notice: Subject to any disclaimer, the term of this patent is extended or adjusted under 35 U.S.C. 154(b) by 968 days.

(21) Appl. No.: 13/981,239

(22) PCT Filed: Feb. 23, 2012

(86) PCT No.: PCT/IB2012/050837
§ 371 (c)(1),
(2), (4) Date: Jul. 23, 2013

(87) PCT Pub. No.: WO2012/114303
PCT Pub. Date: Aug. 30, 2012

(65) Prior Publication Data
US 2013/0304246 A1     Nov. 14, 2013

(30) Foreign Application Priority Data

Feb. 24, 2011  (IT) .................................. BO11A0079

(51) Int. Cl.
*G06F 19/00* (2011.01)
*G05B 13/02* (2006.01)
(Continued)

(52) U.S. Cl.
CPC ........ *G05B 13/02* (2013.01); *A61F 13/15772* (2013.01); *B65H 29/16* (2013.01);
(Continued)

(58) Field of Classification Search
None
See application file for complete search history.

(56) References Cited

U.S. PATENT DOCUMENTS

| 5,045,135 A | 9/1991 | Meissner et al. |
| 6,224,699 B1 | 5/2001 | Bett et al. |
| (Continued) | | |

FOREIGN PATENT DOCUMENTS

| CN | 1329306 | 1/2002 |
| CN | 1663697 | 9/2005 |
| (Continued) | | |

OTHER PUBLICATIONS

Office Action issued by the Japanese Patent Office on Mar. 22, 2016 for counterpart Japanese application No. 2013-554970.
(Continued)

*Primary Examiner* — Wissam Rashid
(74) *Attorney, Agent, or Firm* — Shuttleworth & Ingersoll, PLC; Timothy J. Kilma

(57) ABSTRACT

A method for corrective action on the operation of a line for the production of absorbent sanitary articles, comprises capturing at least one image of each article being fed out of the line; using the image to define first parameters indicating the positioning and/or assembly and/or shape of at least one respective component; detecting a production defect if at least one of the first parameters is outside a respective acceptability range; identifying second, line operating parameters which are used to indicate if the first parameter is outside the respective acceptability range; comparing the line operating parameters with respective third, reference parameters indicating optimum line operation; using the comparison to derive a map of abnormal operating parameters; checking if each combination of abnormal operating
(Continued)

parameters indicates a respective cause of malfunction of the line; defining a respective corrective action.

6 Claims, 2 Drawing Sheets

(51) Int. Cl.
    *A61F 13/15*     (2006.01)
    *G05B 19/418*     (2006.01)
    *B65H 29/16*     (2006.01)
    *B65H 43/04*     (2006.01)
    *G06T 7/00*     (2017.01)

(52) U.S. Cl.
    CPC ....... B65H 43/04 (2013.01); G05B 19/41875 (2013.01); G06T 7/001 (2013.01); *B65H 2301/4451* (2013.01); *B65H 2301/542* (2013.01); *B65H 2553/42* (2013.01); *B65H 2801/57* (2013.01); *G05B 2219/37544* (2013.01); *Y02P 90/22* (2015.11)

(56) References Cited

U.S. PATENT DOCUMENTS 6,856,859 B1 * 2/2005 Bett .................. A61F 13/15772
                                                                                                                      700/222
2004/0030432 A1     2/2004   Popp et al.
2009/0195791 A1     8/2009   Lucia et al.

FOREIGN PATENT DOCUMENTS

| CN | 101482657 | 7/2009 |
|---|---|---|
| JP | H04314443 A | 11/1992 |
| JP | 2002530130 A | 9/2002 |

OTHER PUBLICATIONS

Chinese Office Action and Search Report dated Feb. 25, 2015 from counterpart Chinese App No. 201280010297.9.
International Search Report and Written Opinion dated Mar. 29, 2012 from counterpart application.

* cited by examiner

METHOD FOR CORRECTIVE ACTION ON THE OPERATION OF A LINE FOR THE PRODUCTION OF ABSORBENT SANITARY ARTICLES, SUCH AS NAPPIES FOR BABIES OR INCONTINENCE PADS FOR ADULTS, SANITARY TOWELS OR THE LIKE

This application is the National Phase of International Application PCT/IB2011/050837 filed Feb. 23, 2012 which designated the U.S. and that International Application was published under PCT Article 21(2) in English.

This application claims priority to Italian Patent Application No. BO2011A000079 filed Feb. 24, 2011, which application is incorporated by reference herein.

TECHNICAL FIELD

This invention relates to a method for corrective action on the operation of a line for the production of absorbent sanitary articles.

The absorbent sanitary articles according to this invention are intimate hygiene absorbent articles such as nappies for babies, sanitary towels for women, incontinence pads for adults, or the like.

Hereinafter, without thereby limiting the scope of the invention, explicit reference is made to a line for the production of nappies for babies.

BACKGROUND ART

The prior art processes for the production of nappies for babies are characterised by highly complex construction, and at the same time the nappies have a highly complex structure. For that reason, production is often affected by a high percentage of rejects.

For that reason production lines are suitably monitored, in order to correct, as promptly as possible, any inaccuracies and errors in the operation of the operating stations present on the line, so as to limit the number of rejects.

To do that, the use of a plurality of video cameras is known, positioned along the production line, for capturing images of the nappies during their production. The video cameras are usually positioned at the outfeed of each operating station. An analysis of the images is used to adopt suitable corrective action if the system detects the presence of production errors or faults.

Prior art machines which use production monitoring systems of the type described are particularly expensive and complex due to the need to provide a large number of video cameras, normally equal to the number of operating stations.

Another disadvantage is the fact that the analysis of the images gathered has to be performed by highly complex computers which are therefore very expensive.

DISCLOSURE OF THE INVENTION

The aim of the invention is to provide a method for corrective action on the operation of a line for the production of absorbent sanitary articles, such as nappies for babies or incontinence pads for adults, sanitary towels or the like, which has a low level of complexity, low cost and at the same time allows production errors and rejects to be minimised.

Another aim of the invention is to produce an absorbent article of high quality with a low production cost.

Another important aim of the invention is to provide a method for corrective action on the operation of a line for the production of absorbent sanitary articles, such as nappies for babies or incontinence pads for adults, sanitary towels or the like, which does not require the operator to have advanced technical knowledge in order to solve problems deriving from line operating faults.

Accordingly, the invention fulfils said aims with a method for corrective action on the operation of a line for the production of absorbent sanitary articles, such as nappies for babies or incontinence pads for adults, sanitary towels or the like, whose technical features are clearly described herein.

In particular, according to the invention a method is implemented for corrective action on the operation of a line for the production of absorbent sanitary articles, such as nappies for babies or incontinence pads for adults, sanitary towels or the like, each article comprising a plurality of components which are gradually positioned relative to each other and assembled along the production line; the method being characterised in that it comprises the steps of:
- capturing at least one image of each article being fed out of the line;
- using the image to define first parameters indicating the positioning and/or assembly and/or shape of at least one respective component;
- detecting a production defect if at least one of the first parameters is outside a respective acceptability range;
- identifying second, line operating parameters which are used to indicate if the first parameter is outside the respective acceptability range;
- comparing the line operating parameters with respective third, reference parameters indicating optimum line operation;
- deriving from the comparison a map of parameters indicating abnormal operation;
- checking if each combination of abnormal operating parameters indicates a respective cause of line malfunction, the respective cause being included in a case record of causes of malfunction which is preset and predefined;
- defining, for each cause of malfunction encountered, the corrective action to be adopted in order to eliminate the production defect.

Preferably, the corrective action is displayed in the form of instructions on a display for subsequent guided action by an operator.

Preferably, the instructions contain a sequence of step-by-step instructions for guiding the operator to correct the defect.

Alternatively, the corrective action is automatically converted into action controlling actuator means acting on the production line for adjusting the operating parameters.

BRIEF DESCRIPTION OF THE DRAWINGS

The advantages of the invention are more apparent from the detailed description which follows, with reference to the accompanying drawings which illustrate a preferred, non-limiting example embodiment of the invention and in which.

DETAILED DESCRIPTION OF THE PREFERRED EMBODIMENTS OF THE INVENTION

Figure 1:
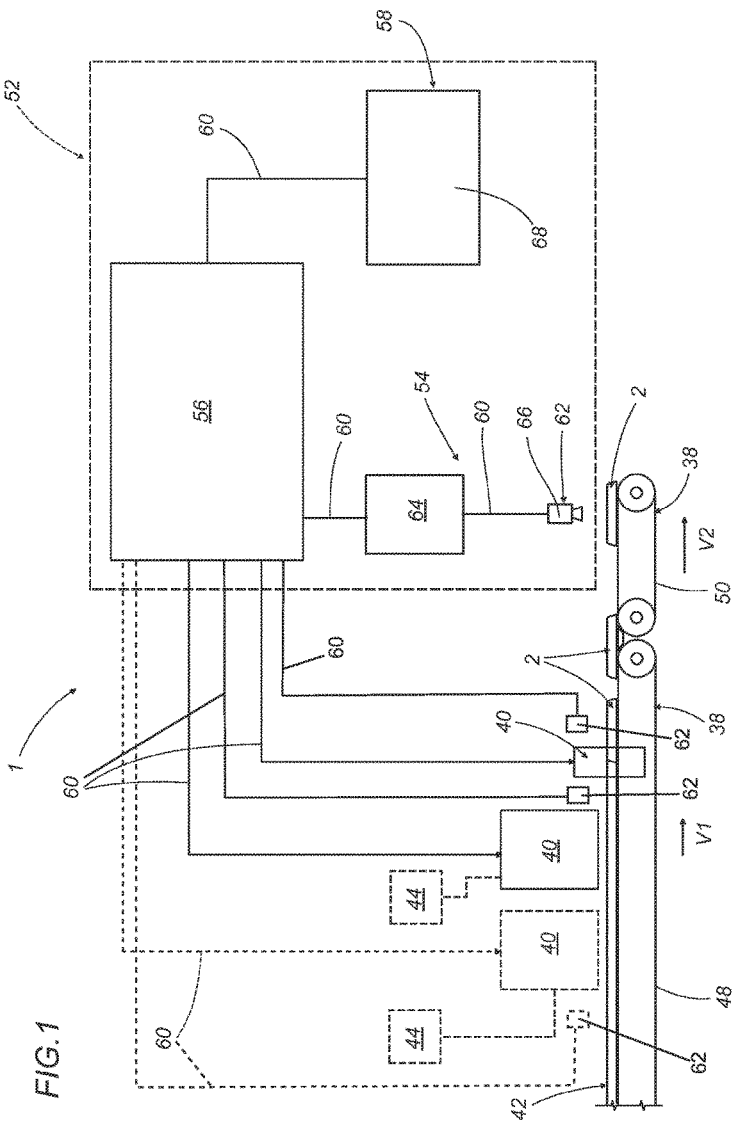
FIG. 1 is a schematic front view of a production line according to the invention.
Figure 2:
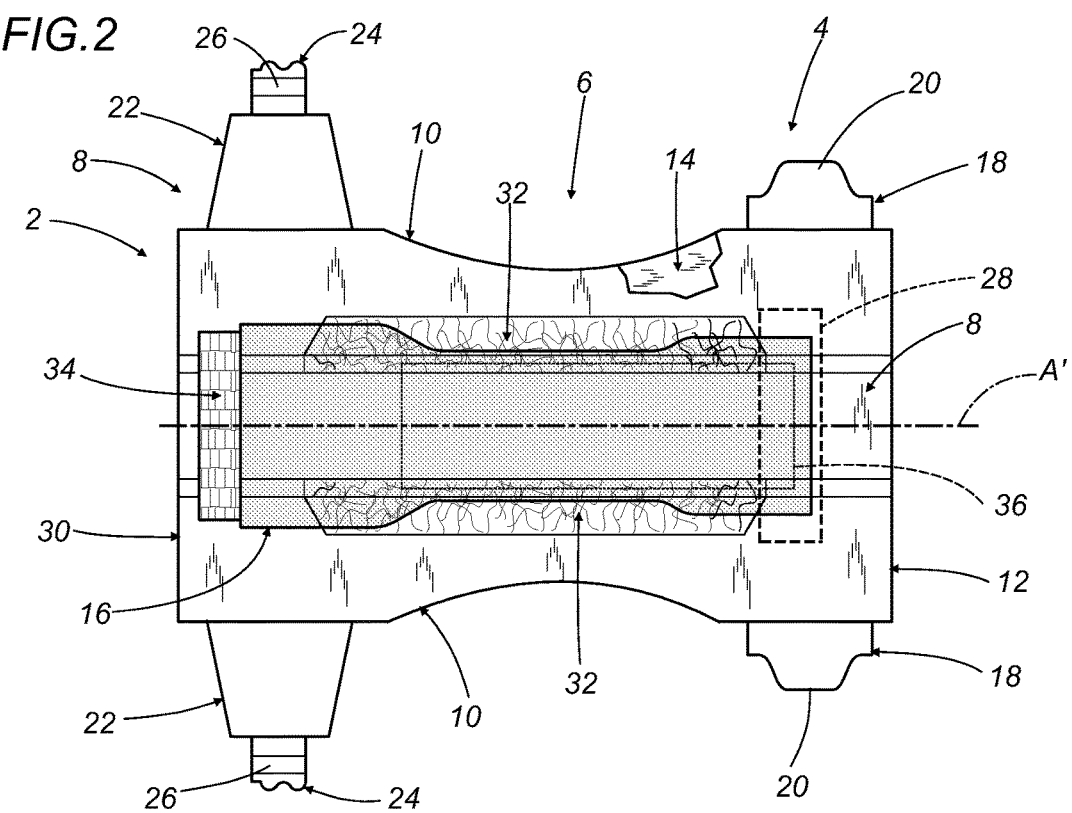
FIG. 2 is a plan view of a schematic example of an absorbent sanitary article made by the line in FIG. 1.

As illustrated in FIG. 1, the numeral 1 denotes a line for the production of absorbent sanitary articles 2, the article shown in more detail in FIG. 2. Specifically, FIG. 1 shows the end portion of a production line 1.

The article 2 in FIG. 2 has a substantially rectangular shape. In the specific example the articles 2 are nappies for babies, however, within the scope of this invention and according to alternative embodiments which may be immediately deduced from the context and description, the articles 2 may be sanitary towels for women, or they may be incontinence pads for adults.

The articles 2 comprise, aligned along their longitudinal axis labelled A', a front portion 4, a central portion 6 and a rear portion 8. At the central portion 6 there is a recess 10, or leg opening, formed by two arched stretches which are symmetrical relative to the axis A'.

The absorbent articles 2 are formed by a plurality of elements, which may be separated into first basic components and second additional components. In particular, the basic components are put together or assembled in such a way as to form a basic article 2, whose components are arranged according to a preset and predefined pattern. Similarly, the additional components are applied to the basic article during and/or after it has been formed, according to a preset and predefined pattern, in such a way as to produce a finished article 2.

The first basic components comprise a first sheet 12 of permeable material (non-woven fabric) and a second sheet 14 of impermeable material, which are respectively designed to form the inner face and the outer face of the article 2.

The sheets 12 and 14 are superposed on top of one another and a third main element consisting of an absorbent pad 16 is interposed between them. The pad 16 is made of cellulose fibre and granules of a super absorbent polymer (SAP) which are dispersed in the latter.

The additional components, which may vary in number and form, are hereinafter described with reference to the absorbent sanitary article 2 illustrated in FIG. 2.

The numeral 18 denotes two first shaped wings, each comprising a respective lobe 20, which are fixed to the inner face of the second, impermeable sheet 14 and project transversally to the axis A' from the front portion 4 of the article. The numeral 22 denotes two shaped fastening wings, parallel with the first wings 18, and extending from the rear portion 8 of the article.

Applied to each of the second, fastening wings 22 there is a third small wing 24 equipped with an adhesive strip 26, running parallel with the axis A', designed to adhere, in use, to a corresponding front strip 28 applied to the front portion 4 of the outer face of the second sheet 14. The wings 22 equipped with the small wings 24 form, together with the front strip 28, means for fastening the article 2.

According to an alternative embodiment, the adhesive strip 26 may be substituted with a strip of Velcro®.

Sealed to the sides of the first sheet 12 of permeable material there are two strips 30 of impermeable material for thickening and expanding its longitudinal edges. The strips 30 have an elasticated portion 32 at an intermediate stretch of them.

A further additional component is an elastic band 34 applied, transversally to the axis A', to the inner face of the second sheet 14 at the rear portion 8 of the article 2.

On the inner face of the first sheet 12 of permeable material, in contact with the absorbent pad 16 and sealed along the border of the latter, there is a sheet 36 of absorbent material, called the "acquisition layer", which is designed to render uniform the absorption by the surface of the absorbent pad 16.

With reference to FIG. 1, the line 1 comprises feed means 38 for the absorbent article 2 and a plurality of operating stations 40 of the known type which produce the article 2.

The term operating station 40 refers to a station comprising at least one operating unit designed to perform a precise operation on the article 2 during production. Such operations may comprise, preferably, the addition of material constituting the basic components and the additional components, cutting of materials to produce the individual components or to produce shapes for components already applied, sealing of components, application of additional components on the basic article, and the like.

In particular, FIG. 1 shows the end portion of the line 1, in which the final operating station 40, positioned at the line 1 outfeed, is preferably a station for cutting a continuous web 42 of articles 2 which are joined together, resulting from the production process, into individual absorbent articles 2.

The article 2 feed means 38 may preferably comprise a plurality of conveyor belts. In particular, the FIG. 1 shows a first conveyor belt 48 and a second conveyor belt 50. The second conveyor belt 50 is preferably positioned at the outfeed of the final operating station 40 and has a speed v2 which is greater than the speed v1 of the first belt 48, in such a way that it can space out the individual articles 2 just cut.

Associated with the line 1 there is a system 52 for monitoring production, for checking the quality of the articles 2 fed out of the line 1 and for implementing corrective action relative to any faults or defects which arose during production.

Examples of defects or faults in production are described below, with particular reference to defects arising during assembly, application and forming of the first basic components and the second additional components.

Figure 3:
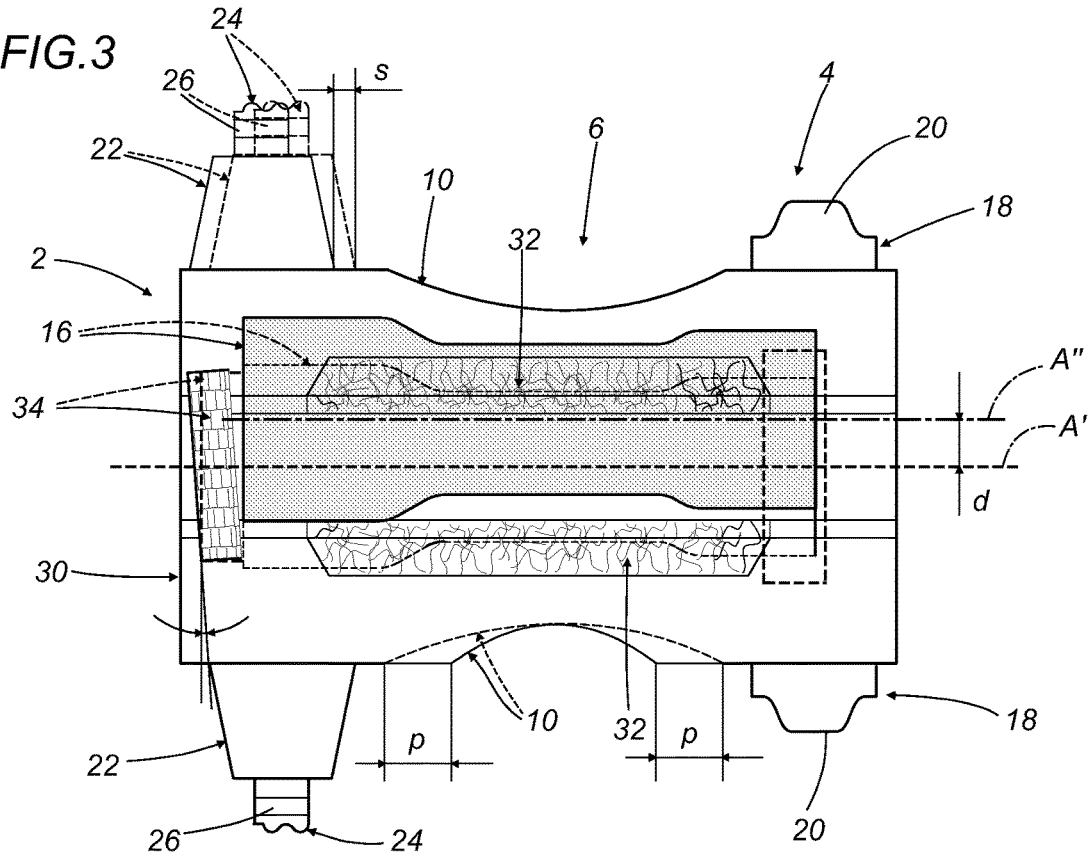
FIG. 3 illustrates the article of FIG. 2, with some parts removed and others modified.

As shown in more detail in FIG. 3, which illustrates the absorbent article 2 of FIG. 2 with several components incorrectly positioned relative to the correct positions indicated with a dashed line, typical faults in the finished article 2 may include: incorrect alignment of the absorbent pad 16, incorrect orientation of the front strip 28, incorrect positioning of the fastening wings 22 and incorrect execution of the recess 10 cut.

With reference to FIG. 1, the monitoring system 52 preferably comprises means 54 for inspecting the article 2 for capturing at least one image of each article 2 being fed out of the line.

The monitoring system 52 further comprises a unit 56 for processing features measured from the image by the inspection means 54, means 58 for displaying information about the production line 1 and the article 2, a communication network 60 to allow circulation of the above-mentioned information.

The processing unit 56 preferably comprises an industrial-type computer, not illustrated, able to examine and process the features of the article 2 measured, acquired, by the inspection means 54.

According to the preferred embodiment, the inspection means 54 are positioned close to the line 1 outfeed, downstream of the final operating station 40.

The inspection means 54 comprise at least one sensor 62 for capturing at least one image of the article 2 and acquisition means 64 for the image or images of the article 2.

The sensor 62 may be positioned opposite the belt 50, as illustrated in FIG. 1, for capturing at least one image of each finished article 2, that is to say already separated from the continuous web 42 of articles 2 which are joined to each other, or, according to an alternative embodiment not illustrated but which may be immediately deduced from the context and from FIG. 1, the sensor 62 may be positioned opposite the belt 48 for capturing at least one image of each article 2 when the article has still not been separated from the continuous web 42 of articles 2 which are joined to each other. In both cases, the sensor 62 is positioned at the line 1 outfeed for capturing at least one image of each article 2 already formed in terms of the composition and assembly of its components, both basic and additional.

The sensor 62 preferably takes the form of a linear or matrix video camera 66 designed to perform a scan of the article 2 at the line 1 outfeed.

In a further embodiment the sensor 62 is an infrared sensor.

In a further embodiment the sensor 62 is an ultraviolet sensor.

In a further embodiment the sensor 62 is an X-ray sensor.

In a further embodiment there is a combination of two or more of the sensors 62 indicated above.

During operation, the acquisition means 64 define, using the image or images, first parameters indicating the positioning and/or assembly and/or shape of at least one respective component.

In particular, the first parameters are of the numeric type and are representative of the measured features of the article 2.

The acquisition means 64 comprise, in a preferred embodiment, an electronic control unit for defining the first parameters. The control unit, not illustrated in the accompanying drawings, is associated with at least one respective sensor 62.

The acquisition means 64 send the first parameters processed to the data processing unit 56.

The processing unit 56 assesses whether or not the first parameters lie within a respective acceptability range.

In other words, the acceptability range provides an indication of the extent to which the measured features of the article 2 lie within the optimum tolerance values considered acceptable, and therefore, allows one to understand if the products 2 are affected by faults or defects.

The processing unit 56 assesses whether or not at least one first parameter is outside the respective acceptability range. If so, the unit 56 identifies the presence of a production defect.

Examples of possible production defects are shown in FIG. 3, which indicates, relative to the correct position of the component traced with a dashed line, the linear deviation s value, in a direction parallel with the axis A', of a second fastening wing 22; the linear deviation d value of the absorbent pad 16, relative to its own longitudinal axis A", in a direction transversal to the axis A' of the article 2; the angular deviation α value of the front strip 28; the deviation p of the starting and end points of the recess 10 cut.

If there is a defect in the article 2, the processing unit 56 identifies second, line 1 operating parameters which are used to indicate if the first parameter is outside the respective acceptability range.

The second operating parameters indicate the operating state of a respective operating station 40 in the line 1. In particular, the processing unit 56 identifies the respective operating stations 40 of the line 1 which give the first parameters that are generating the defect.

Preferably, the processing unit 56 sends, via the communication network 60, information about the above-mentioned operating stations 40 to the display means 58.

Specifically, the second operating parameters are linked to the process for positioning, assembly and/or forming of the components of the article 2.

For example, typical process parameters may comprise the tension of added materials, vacuum level of suction units, level of static electricity present, state of the air jets, impact energy level of the cutting means, level of cleanness of the components, and others.

Once the second parameters have been identified, the processing unit 56 compares the second parameters with respective third, reference parameters indicating optimum line 1 operation.

The operating parameters used in the comparison by the processing unit 56 are monitored by sensors, not illustrated in the accompanying drawings, which are mounted on each operating station 40.

After the comparison between the second and third parameters, the processing unit 56 derives a map of abnormal operating parameters. The map substantially represents a set of second operating parameters which deviate from the third reference parameters, and therefore are "abnormal" since they do not define optimum line 1 operation and consequently result in non-optimum quality of the absorbent article 2.

Then, the processing unit 56 checks if each combination of abnormal operating parameters indicates a respective cause of line 1 malfunction. In particular, the cause is searched for in a case record of causes which is preset and predefined, present in a database.

The case record is preferably the result of modelling based on the study of the most frequently encountered defects and problems in lines for the production of absorbent products, and therefore the consequent possible causes which generate such defects.

The implementation of templates created based on said information, preferably using FMEA-type analysis, allows the processing unit 56 not just to form a database of causes of defects that may occur, including the above-mentioned case record, but also to trace the operating station 40 which may have generated the defect.

For that purpose the processing unit 56 is logically connected to sensors 62, with which each of the line 1 operating stations 40 is equipped.

Moreover, the processing unit 56 generates an alarm signal which warns that the line 1 is producing an article 2 which has defects or that there are line 1 operating faults present.

The alarm signal is sent, via the communication network 60, to the display means 58 so as to alert an external operator to the presence of the production fault.

After identifying the causes relative to the process for execution of the various operations which generated the faults on the article 2 during production, the processing unit 56, based on the causes identified, generates the correction action necessary for correcting the defect.

Said corrective action is also sent to the display means 58 and made known to the external operator, who promptly applies it and restores correct line 1 operation.

In an alternative embodiment, the corrective action is automatically converted into action controlling actuator means 44 acting on the production line 1 for adjusting the above-mentioned second operating parameters.

More precisely, advantageously, it is possible to implement in the processing unit 56 a set of data relating to problems and respective causes which may not require the intervention of the external operator, but which may also be resolved automatically by the operating stations 40 themselves, using said actuator means 44, with which the operating stations 40 can be equipped.

The display means 58 comprise a display 68, representing a communication interface between the line 1 and the operator. The display 68 may advantageously be of the touch-screen type, allowing the operator not just to view the various information about production, but also to intervene in person, as in the case just described of a fault which occurred, being able to manually enter, for example, the correct process parameter values.

The processing unit 56 sends the display 68 all of the information needed by the operator to restore correct line 1 operation. Advantageously, the processing unit 56 preferably sends the display 68 the corrective action relating to the fault encountered. Moreover, even the alarm signal is preferably sent by the processing unit 56 to the display 68.

The corrective action displayed for the operator on the display 68 comprises a sequence of step-by-step instructions for guiding the operator to correct the defect. These instructions are a guide for the operator on where and how to intervene in order to restore correct line 1 operation. Advantageously, the corrective action provides all of the information useful and necessary to the operator, such as which tools to use, which specific operating station 40 must be worked on, which precise operations must be performed on each individual station 40, and similar information. Therefore, the action of the operator is guided, advantageously allowing him to freely consult the instructions.

A monitoring method such as that described brings many advantages.

First, the operator, even if not having an in-depth knowledge of the line component-parts, can rapidly carry out maintenance work on the line, since all of the information needed is promptly supplied.

Moreover, the operator is able to perform the corrective action without making mistakes, since simple, clear and detailed information is provided.

Moreover, the monitoring system, which implements the method according to the invention, is less expensive and is simpler in terms of construction, using fewer sensors for product monitoring, compared with prior art systems, and using less complex systems for processing the data gathered. Even from a computing viewpoint the system is simpler, since the number of pieces of information which the data processing system must manage is lower.

The line in which the method according to this invention is implemented also allows the production of absorbent articles with more economical production and with higher quality.

The invention described herein is susceptible of industrial application and may be modified and adapted in several ways without departing from the scope of the inventive concept. Moreover, all the details of the invention may be substituted by technically equivalent elements.

The invention claimed is:

1. A method for corrective action on an operation of a production line for producing an absorbent sanitary article comprising a plurality of components which are gradually positioned relative to each other and assembled along the production line; comprising:
   providing the production line with:
   a feed device for the absorbent sanitary article and a plurality of operating stations which produce the absorbent sanitary article, each of the plurality of operating stations including an operating station sensor;
   a monitoring system for monitoring production associated with the production line for checking a quality of the absorbent sanitary article fed out of the production line and for implementing corrective action relative to any faults or defects which arose during production;
   the monitoring system comprising an inspection system for inspecting the absorbent sanitary article and capturing an image of the absorbent sanitary article being fed out of the production line;
   the inspection system comprising a sensor for capturing the image of the absorbent sanitary article and an acquisition device for the image;
   the monitoring system comprising a processing unit for processing features measured from the image by the inspection system, a displaying device for displaying information about the production line and the absorbent sanitary article, and a communication network connecting the inspection system, processing unit and displaying device for circulation of information between inspection system, processing unit and displaying device;
   the processing unit being logically connected to the operating station sensors;
   the acquisition device using the image to define a first set of parameters indicating at least one chosen from positioning and assembly of at least one respective component to form at least one chosen from a basic article and a shape of the at least one respective component;
   the processing unit assessing whether the first set of parameters lie outside a respective acceptability range, and if so, identifying a presence of a production defect;
   the processing unit identifying the respective operating stations of the production line which provide the first set of parameters that are generating the production defect;
   the processing unit identifying a second set of line operating parameters which are used to indicate if the first set of parameters is outside the respective acceptability range;
   the second set of line operating parameters indicating an operating state of a respective operating station in the production line; the second set of line operating parameters being linked to the process for at least one chosen from positioning, assembling and forming of the components of the absorbent sanitary article;
   the second set of line operating parameters used in the comparison by the processing unit being monitored by the operating station sensors;
   the processing unit comparing the second set of line operating parameters respectively with a third set of reference parameters indicating optimum line operation;
   the processing unit deriving from the comparison a map of parameters indicating abnormal operation; the map representing a deviation set of the second set of line operating parameters which deviate from the third set of reference parameters, and therefore are abnormal since the deviation set defines non-optimum line operation and consequently results in non-optimum quality of the absorbent sanitary article;
   the processing unit checking if each combination of abnormal operating parameters of the map indicates a respective cause of line malfunction, the respective cause being included in a case record of causes of malfunction which is pre-set and predefined;
   after identifying the causes relative to the process for execution of the various operations which generated the faults on the absorbent sanitary article, the processing unit, based on the causes identified, generating a correction action necessary for correcting the defect.

2. The method according to claim 1, and further comprising displaying the corrective action as instructions on a display for subsequent guided action by an operator.

3. The method according to claim 2, and further comprising providing the instructions with a sequence of step-by-step instructions for guiding the operator to correct the defect.

4. The method according to claim 1, and further comprising automatically converting the corrective action into action controlling at least one actuator acting on the production line for adjusting the operating parameters.

5. The method according to claim 1, and further comprising providing that the sensor is a video camera.

6. The method according to claim 1, and further comprising providing that the case record of causes of malfunction is contained in a pre-set and predefined database.

* * * * *